US006713022B1

(12) United States Patent
Noolandi et al.

(10) Patent No.: US 6,713,022 B1
(45) Date of Patent: Mar. 30, 2004

(54) DEVICES FOR BIOFLUID DROP EJECTION

(75) Inventors: Jaan Noolandi, Mississauga (CA); David A. Horine, Los Altos, CA (US); Babur B. Hadimioglu, Mountain View, CA (US); Richard H. Bruce, Los Altos, CA (US); Joy Roy, San Jose, CA (US); Scott A. Elrod, La Honda, CA (US)

(73) Assignee: Xerox Corporation, Stamford, CT (US)

( * ) Notice: Subject to any disclaimer, the term of this patent is extended or adjusted under 35 U.S.C. 154(b) by 1 day.

(21) Appl. No.: 09/724,987

(22) Filed: Nov. 22, 2000

(51) Int. Cl.[7] .................................................. B41J 2/175
(52) U.S. Cl. ........................... 422/100; 347/86; 347/87
(58) Field of Search ..................... 422/100; 347/47, 347/54, 46, 68, 86, 87

(56) References Cited

U.S. PATENT DOCUMENTS

| | | | |
|---|---|---|---|
| 4,115,789 A | | 9/1978 | Fischbeck |
| 4,518,973 A | * | 5/1985 | Tazaki |
| 4,633,274 A | | 12/1986 | Matsuda |
| 5,201,026 A | * | 4/1993 | Tsuiki |
| 5,250,962 A | * | 10/1993 | Fisher et al. |
| 5,338,688 A | | 8/1994 | Deeg et al. |
| 5,465,629 A | * | 11/1995 | Waylett, Jr. |
| 5,475,279 A | | 12/1995 | Takeuchi et al. |
| 5,565,113 A | | 10/1996 | Hadimioglu et al. |
| 5,614,929 A | * | 3/1997 | Dangelo et al. |
| 5,631,678 A | | 5/1997 | Hadimioglu et al. |
| 5,643,379 A | | 7/1997 | Takeuchi et al. |
| 5,658,802 A | | 8/1997 | Hayes et al. |
| 5,796,417 A | * | 8/1998 | Nobel |
| 5,798,779 A | * | 8/1998 | Nakayasu et al. ............ 347/46 |
| 5,877,580 A | | 3/1999 | Swierkowski |
| 5,933,170 A | | 8/1999 | Takeuchi et al. |
| 5,943,075 A | * | 8/1999 | Lee et al. ..................... 347/54 |
| 5,953,028 A | * | 9/1999 | Nobel et al. |
| 5,958,342 A | | 9/1999 | Gamble et al. |
| 6,001,309 A | | 12/1999 | Gamble et al. |
| 6,114,122 A | | 9/2000 | Besemer et al. |
| 6,242,266 B1 | * | 6/2001 | Schleifer et al. ............ 436/518 |
| 6,290,340 B1 | | 9/2001 | Kitahara et al. |
| 6,365,378 B1 | * | 4/2002 | Hirota et al. |
| 6,384,210 B1 | * | 5/2002 | Blanchard .................. 536/25.3 |
| 6,407,437 B1 | | 6/2002 | Burger et al. |
| 6,599,479 B1 | * | 7/2003 | Kietzmann et al. |
| 2002/0115101 A1 | * | 8/2002 | Hirota, et al. |
| 2003/0012892 A1 | | 1/2003 | Lee et al. |
| 2003/0040107 A1 | * | 2/2003 | Hirota, et al. |
| 2003/0048341 A1 | | 3/2003 | Mutz et al. |
| 2003/0104465 A1 | * | 6/2003 | Hirota, et al. |

FOREIGN PATENT DOCUMENTS

| | | | |
|---|---|---|---|
| DE | 197 54 000 | * | 6/1999 |
| EP | 0 294 172 A2 | | 12/1988 |
| EP | 0 493 102 A1 | | 1/1992 |
| EP | 0 469 444 A1 | | 2/1992 |
| EP | 0 622 201 A2 | * | 11/1994 |
| EP | 0 683 048 A2 | | 11/1995 |
| EP | 0 572 231 B1 | | 10/1996 |
| EP | 0 865 824 A1 | | 9/1998 |
| EP | 0 872 346 A1 | * | 10/1998 |
| EP | 1 008 451 A2 | | 6/2000 |
| EP | 1 093 855 A2 | * | 4/2001 |
| WO | WO 00/24511 | | 5/2000 |

OTHER PUBLICATIONS

Experts in Microdispensing & Precision Printing (MicroFab Technologies, Inc.) http://www.microfab.com—last updated Jun. 12, 2000.
Goldmann et al., "DNA–Printing:Utilzation of a Standard Inkjet Printer For the Transfer of Nucleic Acids to Solid Supports", J. Biochem. Biophys. Methods 42 (2000) 105–110 XP–000889698.

* cited by examiner

*Primary Examiner*—Jan Ludlow
(74) *Attorney, Agent, or Firm*—Fay, Sharpe, Fagan, Minnich & McKee, LLP

(57) ABSTRACT

A biofluid drop ejection unit for ejecting biofluid drops. A biofluid drop ejection mechanism of such a unit includes a transducer, which generates energy used to emit the biofluid drop. Further provided is a reagent cartridge or biofluid containment area which holds the biofluid. The reagent cartridge or biofluid containment area is configured to hold low volumes of biofluid and to avoid contamination of the biofluid. The reagent cartridge or biofluid containment area is in operational connection with the drop ejection mechanism such that upon operation of the drop ejection mechanism, biofluid drops are emitted. The biofluid drop ejection mechanism is a high efficiency device, and may be configured as two separate pieces or as a single disposable unit.

20 Claims, 10 Drawing Sheets

DEVICES FOR BIOFLUID DROP EJECTION

BACKGROUND OF THE INVENTION

The present invention is directed to devices for ejecting biofluid drops, and more particularly to such devices designed to maximize usage efficiency and eliminate unintended contamination of the biofluid drops being ejected from the devices.

In existing drop ejection devices attention to fluid contamination has not been a high priority. For example, in the printing industry issues of contamination have focussed on avoiding unwanted mixing between different inks, in order to maintain intended ink color, and stopping debris from falling into the ink. However, in other environments avoiding contamination of the ejected fluid is a critical consideration. For example, many biological, genetic, pharmaceutical, medical, among other scientific tests, employ sequences or arrays of biofluid drops upon which the tests are to be performed. In these experiments, contaminated drops would result in unreliable, and therefore unusable test results.

In some testing applications several thousand biofluid drops are deposited onto a single substrate in the form of a biological assay. These biological assays will each contain a variety of unique biofluids. For example, in current biological testing for genetic defects and other biochemical aberrations, thousands of the individual fluids are placed on a glass substrate at different well-defined locations. Thereafter, additional depositing fluids may be deposited on the same locations. This printed biological assay is then scanned with a laser in order to observe changes in a physical property. In these situations, it is critical the drop ejection device not be a source of contamination or permit cross-contamination between biofluids. Thus, while existing drop ejection devices commonly employ a single fluid reservoir for multiple ejector mechanisms, this may not be an acceptable design for a drop ejection device emitting biofluids.

Further, the biofluids used in such experiments are extremely costly. In many existing drop ejection devices the volume of fluid in the reservoir and ejector assembly are much larger than what is required for making a biological assay. This unnecessary use of biofluids results in an increased cost of the test. Thus, existing processes for generating these testing sequences or arrays are time consuming, wasteful of the biofluids, of limited accuracy, and economically expensive.

It has, therefore, been determined to be desirable to provide a biofluid drop ejection mechanism which avoids contamination between the drop ejection mechanism and the biofluids, as well as cross-contamination between different biofluids. It is also considered desirable to provide a mechanism which is capable of delivering microvolumes of biofluid in a highly precise and efficient manner, and with differing amounts of volume dependant upon the biofluid being deposited and/or the intended use of the ejected drop.

SUMMARY OF THE INVENTION

A biofluid drop ejection unit for ejecting biofluid drops. A biofluid drop ejection mechanism of such a unit includes a transducer, which generates energy used to emit the biofluid drop. Further provided is a reagent cartridge or biofluid containment area which holds the biofluid. The reagent cartridge or biofluid containment area is configured to avoid contamination of the biofluid used to eject the biofluid drops. The reagent cartridge or biofluid containment area is in operational connection with the drop ejection mechanism such that upon operation of the drop ejection mechanism, biofluid drops are emitted. The drop ejection mechanism may be configured as a single piece disposable device with the biofluid containment area and transducer integrated, as well as a two-piece device with a transducer separate from a disposable cartridge.

DETAILED DESCRIPTION OF PREFERRED EMBODIMENTS

Figure 1:
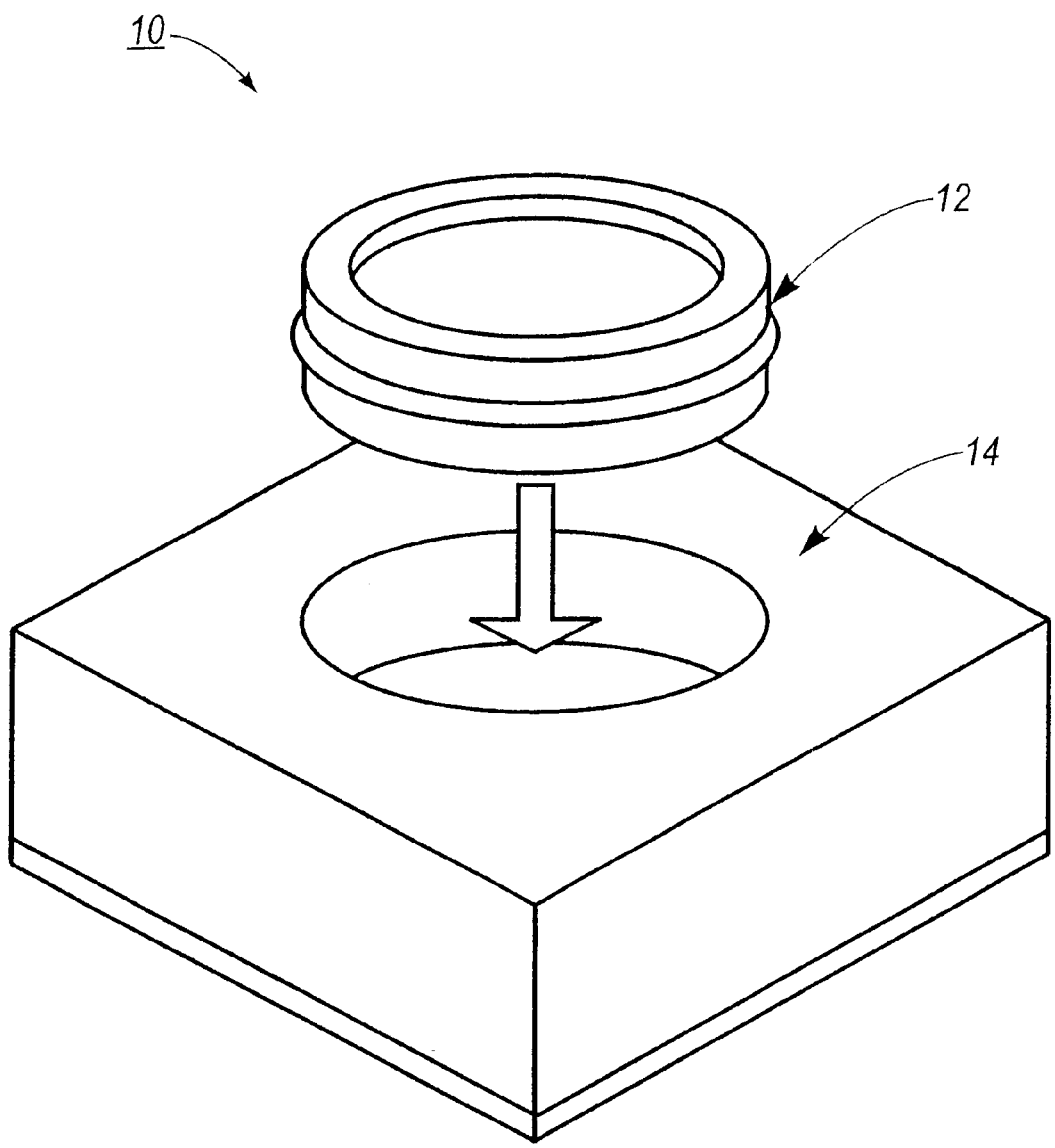
FIG. 1 depicts a reagent cartridge and drop ejection mechanism according to the teachings of the present invention.

FIG. 1 sets forth a two piece acoustic drop ejection unit 10 for ejecting biofluids (also called a reagent). In the present discussion, a biofluid or reagent may be any substance used in a chemical reaction to detect, measure, examine or produce other substances, or is the substance which is to be detected, measured or examined. Unit 10 is configured to have a disposable portion including a reagent cartridge 12, and a reusable portion including an acoustic drop ejection mechanism 14. In FIG. 1, reagent cartridge 12 is shown removed from ejection mechanism 14. In practice, reagent cartridge 12 is inserted within ejection mechanism 14.

Reagent cartridge 12 is configured in such a manner that biofluid contained therein is isolated from the drop ejection mechanism 14 to avoid contamination. The cartridge 12 is constructed as a biochemically inert chamber that contains a quantity of the biofluid. Cartridge 12 and ejection mechanism 14 are precisely aligned in relationship to each other to achieve stable drop ejection and to precisely locate ejected biofluid drops at a desired position on a substrate.

Figure 2:
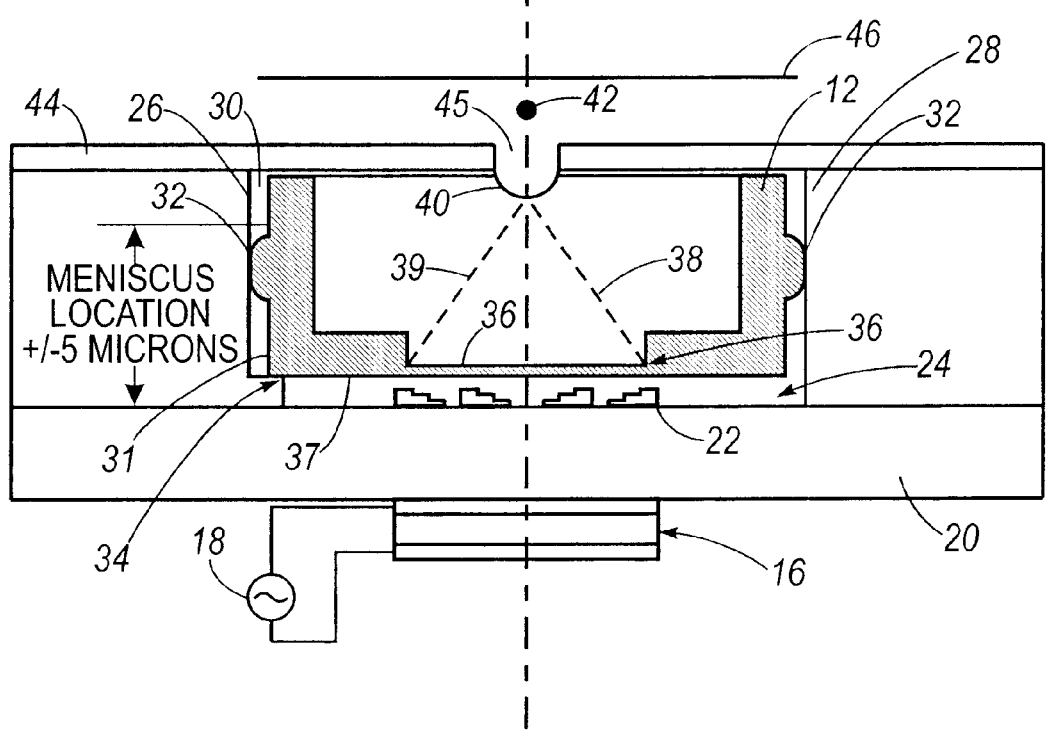
FIG. 2 sets forth a cross-sectional view of the reagent cartridge inserted within an acoustic drop ejection mechanism.

Turning to FIG. 2, depicted is a cross-sectional view of reagent cartridge 12 inserted within acoustic drop ejection mechanism 14. A transducer 16 is supplied with energy by power supply source 18. Transducer 16 is provided on a surface of substrate 20, which in one embodiment may be made of glass. Patterned or located on an opposite surface of substrate 20 is a focusing lens configuration 22 such as a Fresnel lens. It is to be appreciated that other types of focusing configurations may also be used in place of the Fresnel lens.

An acoustic coupling layer 24, which may be an acoustic coupling fluid, is located between Fresnel lens 22 and reagent cartridge 12. The acoustic coupling fluid 24 is selected to have low acoustic attenuation. One type of acoustic coupling fluid having beneficial acoustic characteristics for this application is water.

In an alternative embodiment, connecting layer 24 may be a thin layer of grease. The grease connection will be useful when the joining surfaces are relatively flat in order to minimize the possibility of trapped bubbles.

On top of substrate 20 are walls 26, 28 which define interior chamber 30 within which reagent cartridge 12 is located. Side wall 31 of cartridge 12 includes a seal 32 extending from its outer surface. Seal 32 secures cartridge 12 within chamber 30 and maintains acoustic coupling fluid 24 below seal 32. A precision depth stop 34 holds cartridge 12 at a desired insertion location. A thin membrane 36 is formed on a lower surface 37 of cartridge 12, positioned substationally above Fresnel lens 22. Membrane 36 is an acoustically thin membrane, wherein acoustically thin is defined in this context to mean that the thickness of the membrane is small enough that it passes over 50% of its incident acoustic energy through to biofluid 38 within cartridge 12.

In operation, energization of transducer 16 emits an acoustic wave which travels through substrate 20 to Fresnel lens 22. The lens produces a focused acoustic energy wave 39 that passes through acoustic coupling fluid 24 and membrane 36, reaching an apex at biofluid meniscus surface 40 of biofluid 38. Supplying of the focused energy to surface 40, causes disruptions in the surface, resulting in ejection of a biofluid drop 42 from the cartridge 12 to substrate 43. The biofluid drop ejected can be as small as approximately 15 um in diameter. However, this size limitation is based on the physical components used, and it is to be understood that drops ejected by an acoustic drop ejection unit can be made smaller or larger in accordance with design changes to the physical components.

The surface from which biofluid drops 42 are ejected can be either totally open or contained by an aperture plate or lid 44. The lid 44 will have a suitably sized aperture 45, which is larger than the ejected drop size in order to avoid any interference with drop ejection. Aperture 45 must be sized so that the surface tension of meniscus 40 across aperture 45 sufficiently exceeds the gravitational force on biofluid 38. This design will prevent biofluid 38 from falling from regent cartridge 12 when cartridge 12 is turned with aperture 45 facing down. The aperture down configuration has a benefit of maintaining the biofluid 38 clean from material which may fall from substrate 46, which may be paper, glass, plastic or other appropriate material.

Operation of transducer 16, power supply 18, substrate 20, and lens 22 function in a manner similar to previously discussed drop ejection units used in the field of acoustic ink printing. Such operation is well known in the art.

The foregoing design isolates biofluid 38 within reagent cartridge 12, preventing it from coming into contact with drop ejection mechanism 14, or other potential forms of contamination, such as airborne contamination or contamination from biofluids previously used with the ejection mechanism. Reagent cartridge 12 is separated from acoustic coupling fluid 24 by membrane 36. The entire cartridge may be injection molded from a biologically inert material, such as polyethylene or polypropylene. Cartridge 12 is operationally linked to the acoustic drop emitter mechanism 14 by a connection interface which includes membrane 36 and acoustic coupling fluid 24.

In a specific design of the present invention, the width of reagent cartridge 12 may be approximately 300 microns, and membrane 36 may be 3 microns thick. In this particular embodiment, with a design constraint of a focal acoustic wave length being 300 microns and at an operating frequency of known acoustic drop ejection mechanisms, the meniscus location should be maintained within plus or minus five microns from an ideal surface level.

Power source 18 is a controllably variable. By altering the output of power source 18, energy generated by transducer 16 is adjusted, which in turn may be used to alter the volume of an emitted biofluid 42.

Figure 3A:
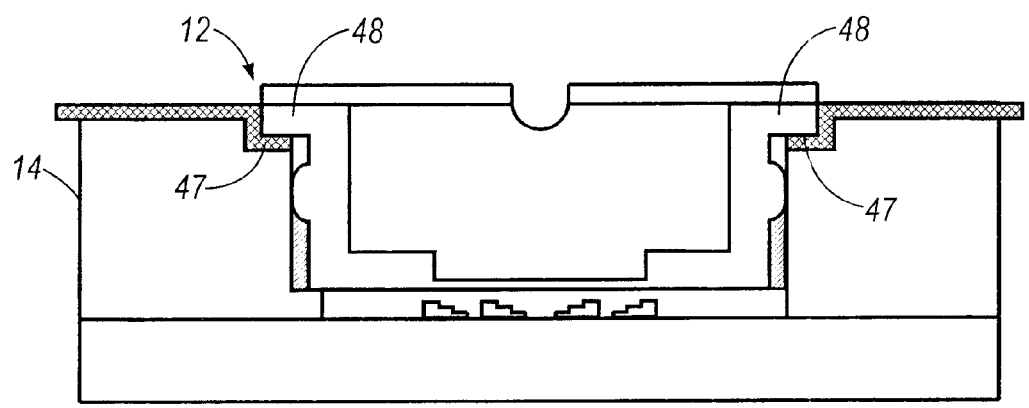
FIGS. 3A and 3B illustrate a technique for inserting and removing the reagent cartridge from the drop ejection mechanism.
Figure 3B:
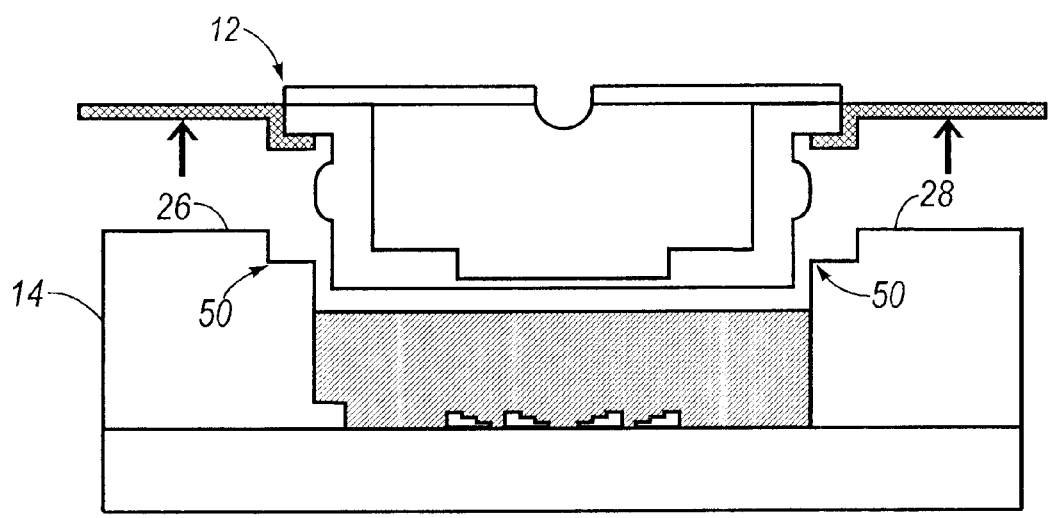
Figure 4A:
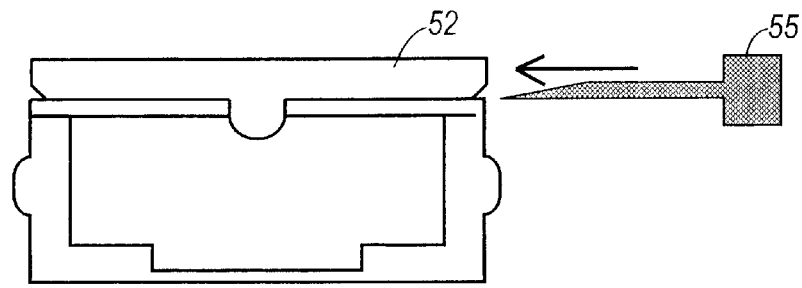
FIGS. 4A and 4B show capped reagent cartridges.
Figure 4B:
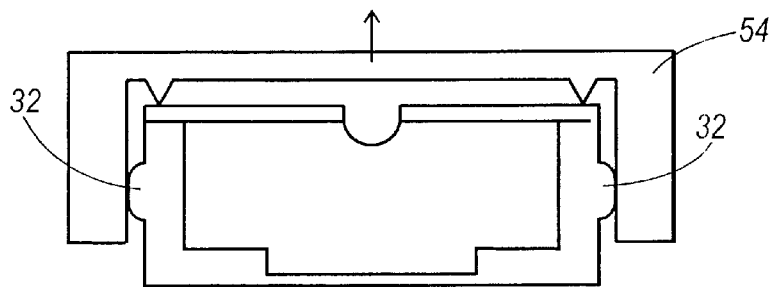

Turning to FIGS. 3A and 3B, as previously noted, the present embodiment is a two piece unit. Therefore, a design feature is that reagent cartridge 12 may be removed and a new reagent cartridge 12 inserted. FIG. 3A, depicts reagent cartridge 12 within drop ejection mechanism 14. One manner to remove cartridge 12 is accomplished by having designed the cartridge with a molded lip 47 connected to cartridge flanges 48. Once a cartridge is depleted of biofluid or otherwise is no longer to be used, it may be removed by lifting molded lip 47 with, an upward force from the acoustic drop emitter mechanism 14 as shown in FIG. 3B. In this embodiment, sidewalls 26, 28 are formed with notches 50 to receive the molded lip portion 47. It is to be appreciated that other designs may be implemented to accomplish the removal of a cartridge. The attachment of molded lip 47 to cartridge 12 may be accomplished after formation of the cartridge, or alternatively, may be part of the injection molding process for construction of the main body of cartridge 12.

With attention to FIGS. 4A and 4B, while in the prior figures reagent cartridge 12 has been depicted as having an open upper surface, to avoid contamination, the cartridge may be formed with a cap or sealing layer such as 52 of FIG. 4A or cap structure 54 of FIG. 4B. In FIG. 4A, cap 52 may be ultrasonically bonded to the cartridge 12. In this situation, it will be necessary to provide some sort of opening device such as a skiving knife 56 for removal of cap 52. Removal of cap 52 is preferably accomplished prior to insertion of cartridge 12 within acoustic drop ejection mechanism 14, however, in some situations removal after insertions may also be useful.

Alternatively, cap 52 may be a thin film material having selected placement of adhesive. Film cap 52 will be removed by a pulling force which may be accomplished by human action or via automation. As a further alternative a press fit cap 54 such as shown in FIG. 4B may be implemented, wherein seal 32 is used to engage the press fit cap 54 in a secure relationship. When cap 54 is to be removed, upward pressure is applied to the press fit cap.

Turning to FIG. 5, it is noted that in previous embodiments lens arrangement 22 was located on the upper surface of glass substrate 20, and therefore is a part of the reusable portion of unit 10. However, in an alternative embodiment, a lens 56 may be configured as a surface of regent cartridge 12. Such an embodiment is achieved by use of a precision molding process for the molding of cartridge 12.

Figure 5:
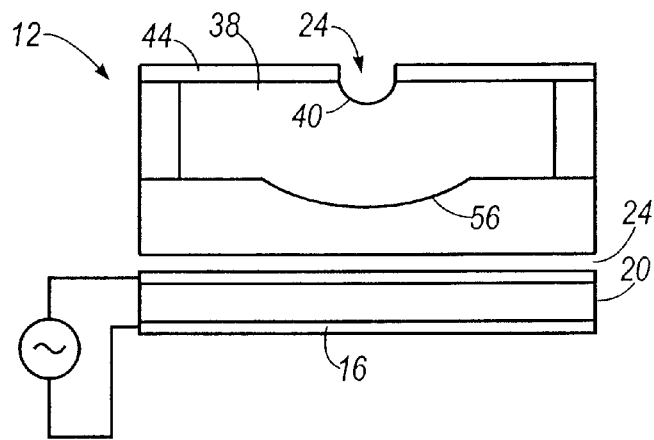
FIG. 5 is a reagent cartridge with an integrated focusing element.
Figure 6:
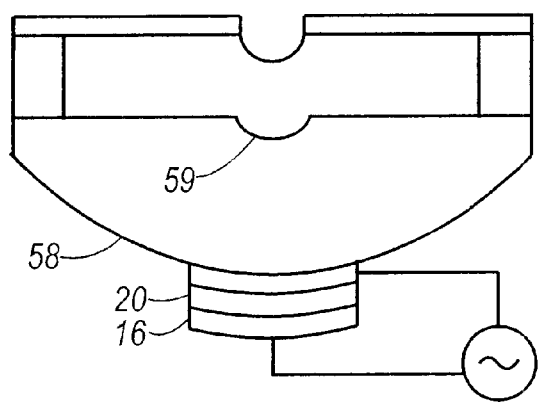
FIG. 6 sets out an embodiment where the transducer is located on a curved lens structure.

In FIG. 6, a further embodiment of the present invention has transducer 16 formed on a lens structure 58. In this configuration the power density on the transducer is lower compared to the standard case when the transducer is on a flat surface. Therefore, a higher power can be applied to the transducer without destroying it due to excessive power. This configuration is particularly useful when the biofluid to be ejected is very viscous or otherwise requires a large amount of acoustic power to eject the biofluid drops. In this embodiment an additional lens 59 may be provided near the biofluid. Under this design the drop ejection unit is a single disposable device. Alternatively the unit of FIG. 6 may also be designed as a two-piece unit. For example lens 56 in FIG. 5, may be used with lens 58 to provide further focusing of the acoustic energy. The curved lens elements 56, 58 and 59 may be a Fresnel lens.

Figure 7:
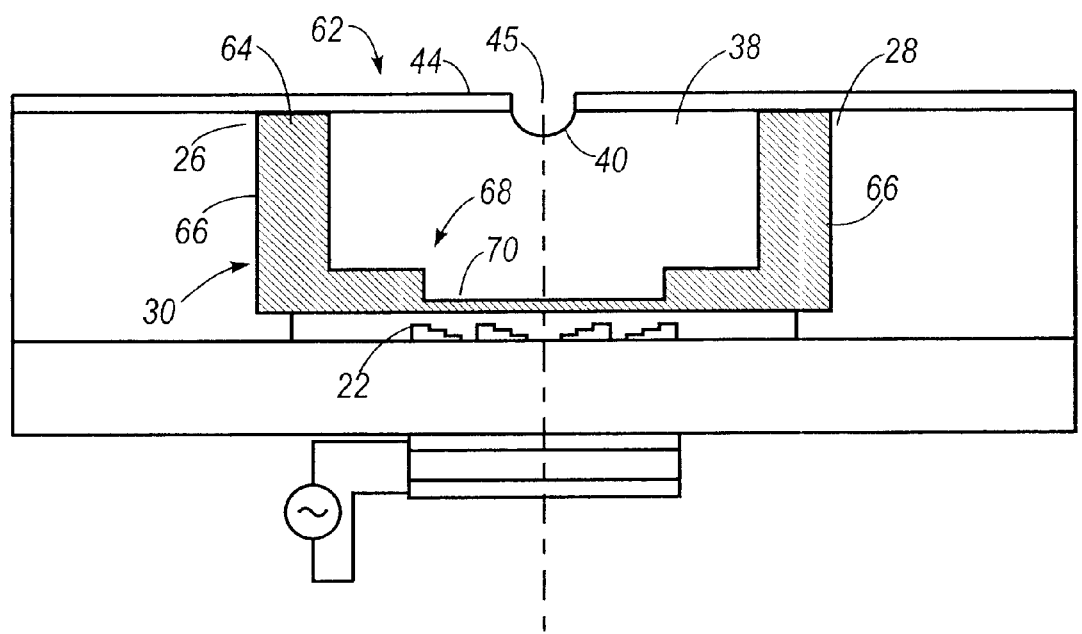
FIG. 7 depicts a single piece acoustic drop ejection mechanism, including a configuration for isolating the biofluids.

Turning to FIG. 7, shown is a single piece biofluid acoustic ejection unit 60. Components similar to the ejection mechanism 14 of FIG. 2, operate in a similar manner and therefore will not be discussed in detail. Distinctions between the two piece biofluid drop ejection unit 10 and the single piece unit 60, include that seal 32 of reagent cartridge 12 is no longer used. Rather, reagent cartridge 62 has side wall 64, with a planar external surface 66 in direct contact with walls 26, 28 of mechanism 14. Therefore, a permanent connection is made between walls 26, 28 to reagent cartridge 62. Such connection may be made during the manufacture of the device via lithographic techniques and/or by use of known adhesion technology. In a further embodiment, lower surface 68, including membrane 70, may be removed, allowing biofluid 38 to come into direct contact with lens 22. Still a further embodiment would be to remove cartridge 62 and supply the biofluid directly into chamber 30, where chamber 30 acts as a non-contaminated biofluid containment area. Under these designs, chamber 30 would be filled with biofluid in a contamination free environment.

It is to be appreciated that the reagent cartridges shown in the foregoing embodiments are simply representative designs of such a component, and that there are many possible variations to the cartridge configuration.

Figure 8:
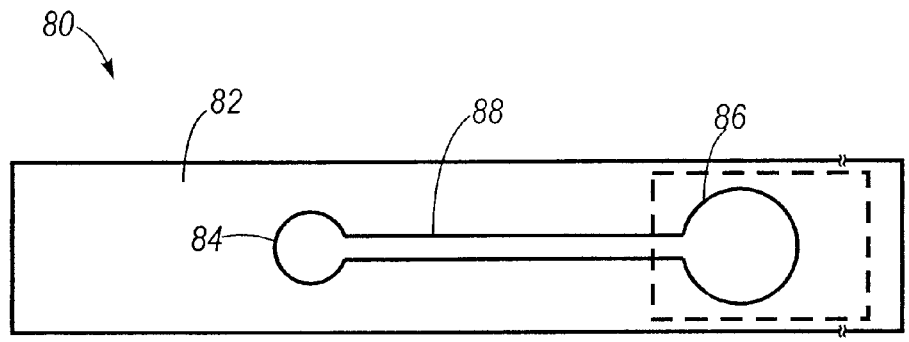
FIGS. 8 and 9 are respective top and side views of an alternative two piece acoustic drop ejection mechanism.
Figure 9:
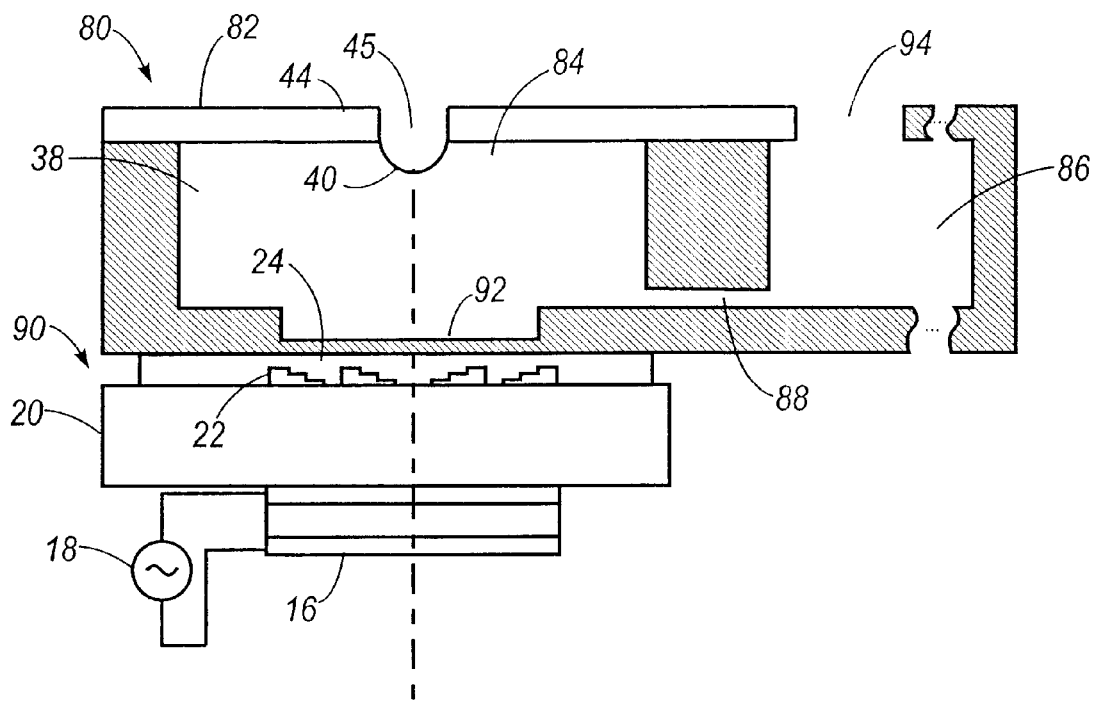

For example, FIGS. 8 and 9 are top and side views, not to scale, of a two piece drop ejection unit 80 employing an alternative reagent cartridge 82 configuration. In addition to ejection reservoir 84 which holds biofluid 38 which is to be directly ejected, a main reservoir 86 is also provided to feed the ejection reservoir 86. A connection path between the ejection reservoir 84 and main reservoir 86 is provided via reservoir connect 88. In this design, as biofluid 38 is ejected from ejection reservoir 84, additional biofluid 38 is supplied via the main reservoir 84 and reservoir connect 88.

FIG. 9 depicts a side view of reagent cartridge 82, in operational arrangement with acoustic drop ejection mechanism 90. Particularly, it is shown that ejection reservoir 84 is located over lens 22, glass substrate 20, and transducer 16 in a manner which allows generated acoustic energy to be focused, and transferred to the ejection reservoir 84 with sufficient energy to emit biofluid drops. In implementing this two piece design, connecting layer 24, such as an acoustic coupling fluid is provided, and a bottom portion of cartridge 80 is formed with a membrane 92, to allow sufficient acoustic energy to be transferred to the ejection reservoir 84.

Capillary action assists in pulling biofluid from main reservoir 86 to ejection reservoir 84, in an initial filling operation when main and ejection reservoirs are empty. However, once the unit is primed and filled to the bottom of aperture 45, a restoring force/surface tension of meniscus 40 is used to pull the biofluid from the main reservoir 86 to the ejection reservoir 84 as drops are ejected. To provide sufficient surface tension at the aperture 45, it is important to have aperture 45 much smaller than filling port 94, so as to avoid a competitive surface tension of filling port 94. The surface tension force of aperture 45 must also be larger than the gravity effect over the height of the structure. By properly balancing these forces, the aperture surface tension continues pulling biofluid into the ejection reservoir 84, to maintain it full, until the main reservoir 86 is depleted.

Figure 10:
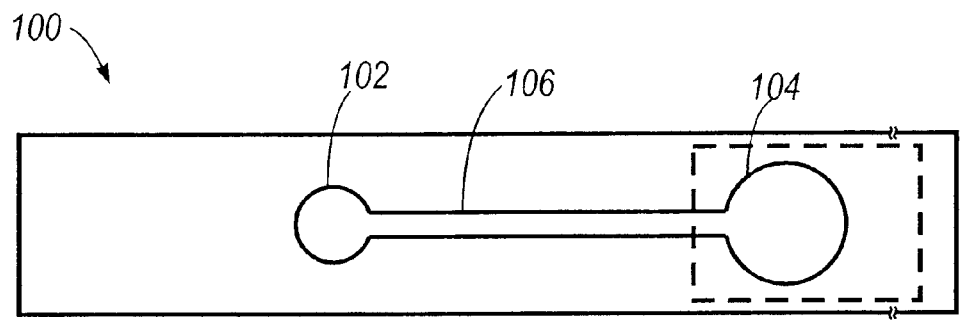
FIGS. 10 and 11 are respective top and side views of an alternative single piece acoustic drop ejection mechanism.
Figure 11:
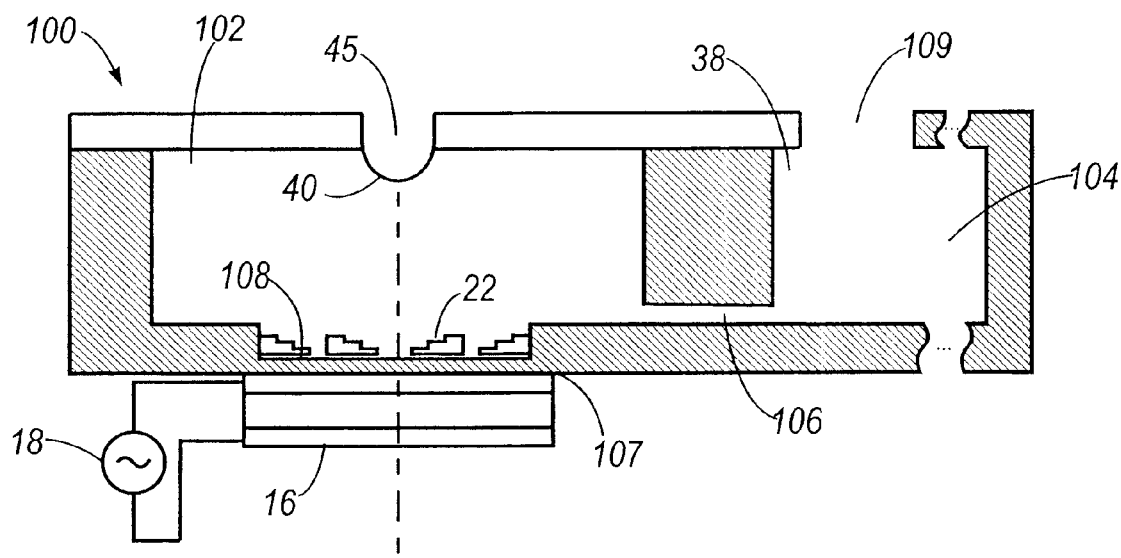

Turning to FIGS. 10 and 11, illustrated is an alternative embodiment for a single piece acoustic drop ejection unit 100. In this figure, ejection reservoir 102 and main reservoir 104 are placed in fluid communication by reservoir connect 106. Biofluid 38 is supplied from main reservoir 104 to ejection reservoir 102 in the same manner as discussed in connection with FIG. 9.

Transducer 16 is in operational connection to a first surface of substrate 107, and lens arrangement 22 is integrated on a second surface of membrane 108, whereby these components are formed as part of the single unit 100. In this embodiment, connecting layer 24 of FIG. 9 is not required due to the single component disposable nature of the present embodiment. In ejection reservoir 102, biofluid comes into direct contact with lens arrangement 22. Main reservoir 104 is filled through filling port 109.

Figure 12:
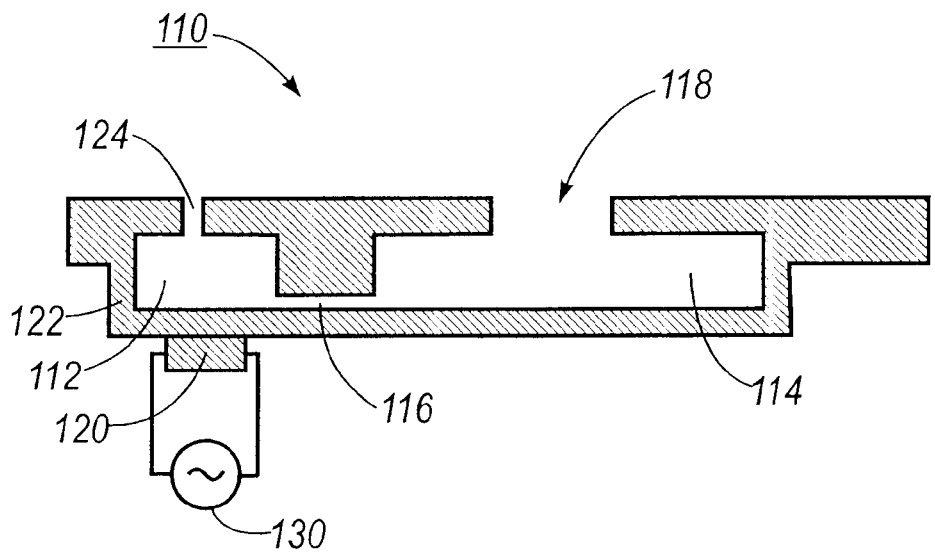
FIGS. 12 and 13 depict a single piece piezoelectric drop ejection mechanism.
Figure 13:
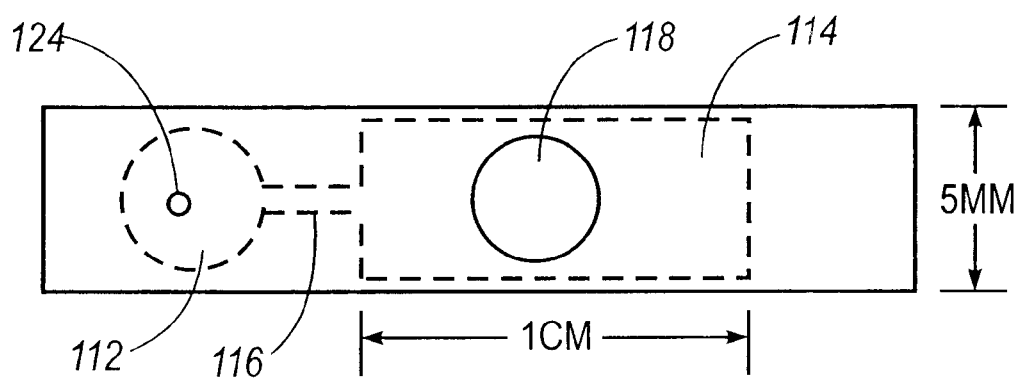

Turning to FIGS. 12 and 13, set forth are side and top views of a single piece disposable piezoelectric drop ejection unit 110. Ejection reservoir 112 is connected to main reservoir 114 via reservoir connect 116. Biofluid is supplied to main reservoir 114 via filling port 118. A piezo actuator 120 is in operational connection to a lower surface 122 of ejection reservoir 112. An upper surface defining the ejection reservoir 112 has formed therein an ejection nozzle 124. A power supply 130 is connected to piezo actuator 120.

In operation piezo actuator 120 is actuated by power supply 130, which in combination with lower surface 122 comprises a unimorph configuration which generates a deflection force in response to an applied voltage. The deflection force is imposed such that the unimorph configuration moves into ejection reservoir 112, thereby altering the volume of ejection reservoir 112, which in turn forces biofluid from the ejection reservoir 122 through nozzle 124 as an ejected biofluid drop. The size of nozzle 124 is a controlling factor as to the size of the ejected drops.

As biofluid drops are emitted from ejection reservoir 112, surface tension in the ejection reservoir causes biofluid located in main reservoir 114 to be drawn through reservoir connect 116 into ejection reservoir 112, thereby replenishing the biofluid level. Similar to the discussion in connection with FIG. 9, sufficient surface tension is obtained by taking into account the size of filling port 118 and the effect of gravity over the height of the structure. In the present embodiment, main reservoir 114 has an internal dimension of 1 cm in length and 2.5 mm in height. The width of the overall piezoelectric drop ejection unit is 5 mm, as shown in FIG. 13. This small size allows for the aggregation of large numbers of ejectors in a system configuration to print multiple biofluids.

As can be seen in FIG. 12, lower surface 122 connected to piezo actuator 120 is integrated into the overall piezoelectric drop ejector unit 110. Under this construction when biofluid of unit 110 is depleted the entire unit 110 may be disposed.

Figure 14:
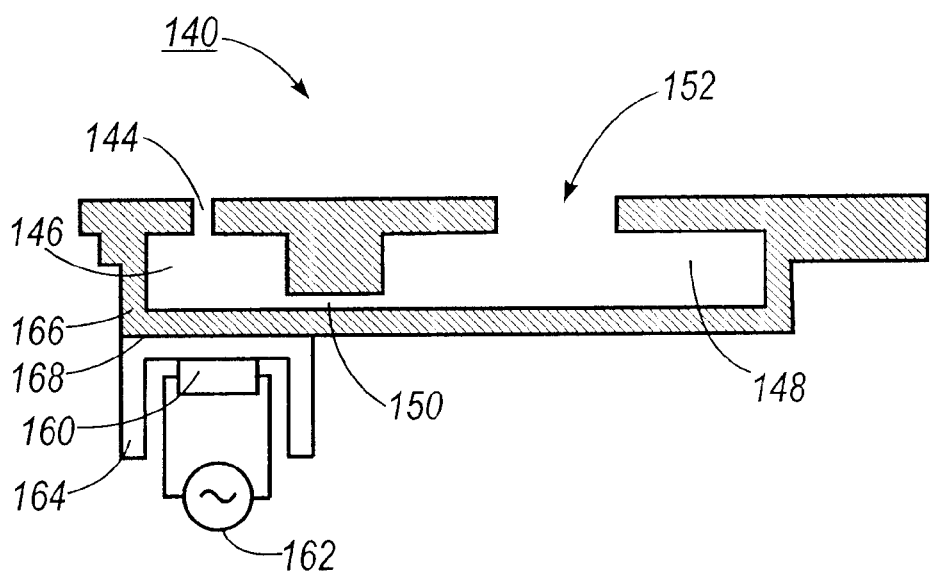
FIGS. 14 and 15 illustrate a two piece piezoelectric drop ejection mechanism.
Figure 15:
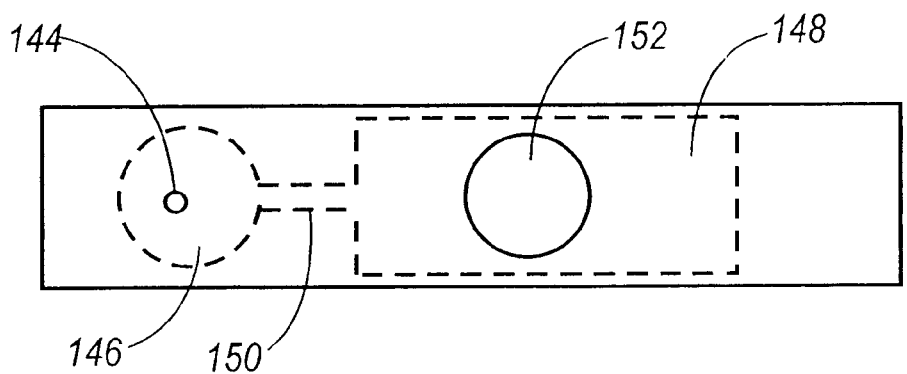

FIGS. 14 and 15, show side and top views of a two piece piezoelectric biofluid drop ejection unit 140 having a disposable portion and a reusable portion. The disposable portion includes a reagent cartridge 142 which has integrated therein an ejection nozzle 144, and an ejection reservoir 146, connected to a main reservoir 148 via a reservoir connect 150. Transmission of biofluid from main reservoir 148 to ejection reservoir 146, via reservoir connect 150 occurs by a capillary feed action. Also included is a filling port 152.

The reusable portion of unit 140 includes actuator 160 powered by a power supply source 162. The piezo actuator 160 is carried on a reusable frame 164.

A flexible membrane lower surface 166, such as a thin layer of polyetholyne, polyemid, or other thin plastic, defines a portion of the ejection reservoir 146 and is bonded to diaphragm upper surface 168 of reusable frame 164. Diaphragm 168, which in one embodiment may be stainless steel, is bonded or otherwise connected to piezo actuator 160 such that diaphragm 168 acts as part of a unimorph structure to create a necessary volume change within ejection reservoir 146 in order to eject a biofluid drop from ejection nozzle 144. Flexible membrane 166 of cartridge 142 acts to transfer the volume change in the reusable portion 164 into the disposable portion.

In a further embodiment, the reusable portion has flexible diaphragm 168 with a piezo actuator on one surface to generate the volume displacement necessary to expel a biofluid drop. A container may be fabricated to place a connecting liquid in contact with the transducer/diaphragm. This liquid assists in transmitting the transducer-induced volume changes to a membrane on a different container surface. The container edges are constructed to make a hermetic seal between the reusable and the disposable parts. The container has a provision for removing (bleeding) air bubbles from the connecting liquid. The opposite surface is open before assembling with the disposable part.

A hermetic seal is provided between the disposable and reusable portions, and the reusable portion is filled with a very thin connecting liquid to transmit the volume changes from the transducer to the disposable portion. To minimize compliance and absorption of volume changes, all air bubbles in this fluid are removed before operation by bleeding them through a bleeding mechanism in the reusable portion. Alternatively, intimate physical contact may be used, such as by application of grease or other material. Connection may also be made by use of a vacuum operation which couples the elements together.

One skilled in the art would understand that other piezo actuator configurations, such as bulk or shear mode designs, may also be used in conjunction with the present invention.

The disclosed biofluid drop ejection units will function using small amounts of biofluid within the main reservoir and the ejection reservoir. For example, the main reservoir may in one instance, when full, contain anywhere from 50 to 150 microliters of biofluid where the ejection reservoir, when full, holds anywhere from 5 to 25 microliters. Thus, it can be seen that operation of the described ejector units are possible using very low volumes of biofluid. The biofluid drops themselves may be in the picoliter range. This is a valuable aspect of these ejector units due to the high cost for many of the biofluids which will be used. Also, since very small volumes of biofluid are required, the use of disposable ejector units become an attractive option.

It is to be appreciated that the described units also operate at a high efficiency whereby little waste of the biofluids will occur. This is both due to the operational aspects of the units themselves and to the fact that small volumes of biofluid are necessary to operate the units. Particularly, if any waste does exist within the system, due to the small amount of biofluid originally used, high efficiencies in operation are nevertheless achievable. In one preferred embodiment high efficiency is defined as use of 80% or more of the biofluid under normal operation.

While the foregoing discussion stated there would be 50–150 microliters in the main reservoir, and 5–25 microliters in the ejection reservoir, these amounts may vary dependant on the drop size being used, the amount of printing to be undertaken, the types of biofluids to be used, as well as other parameters.

A ratio from 2 to 1 to a 10 to 1 of biofluid volume in the main reservoir and the ejector reservoir is a preferred range. This range permits usable surface tension for the drawing of biofluid in certain disclosed embodiments, while also using the small volumes desired. However, it is possible that larger ratios may also be used dependent upon factors including the cost of the biofluid, and the intended use of the ejectors.

FIGS. 7, 11, 12 and 13, disclose disposable drop ejection units which include the aspects of low biofluid volume usage, along with a high efficient use of the biofluid. An additional aspect related to the disposable feature is a benefit obtained in avoidance of contamination. Since the units are disposable, and therefore low-cost, contamination can be avoided simply by disposing of the entire mechanism as opposed to maintaining certain parts of the mechanism which require cleaning operations. Further, the disposable nature and low volume of biofluid will also, for the piezo-electric drop ejection mechanisms, avoid issues as to nozzle clogging. It is to be understood that the longer the nozzle is used, the more likely clogging will occur. This, in actual practice, may lead to undesirable satellite drops of biofluids landing at improper locations thereby causing contamination of the output results.

In piezoelectric drop ejection mechanisms initial operation may not produce intended drop output. Particularly, when air bubbles exist within the ejection reservoir, non-spherical drops, or drops which are not of a proper consistency or size may be ejected and more likely no drops will be produced. Therefore, a priming of the ejection unit is desirable.

Figure 16:
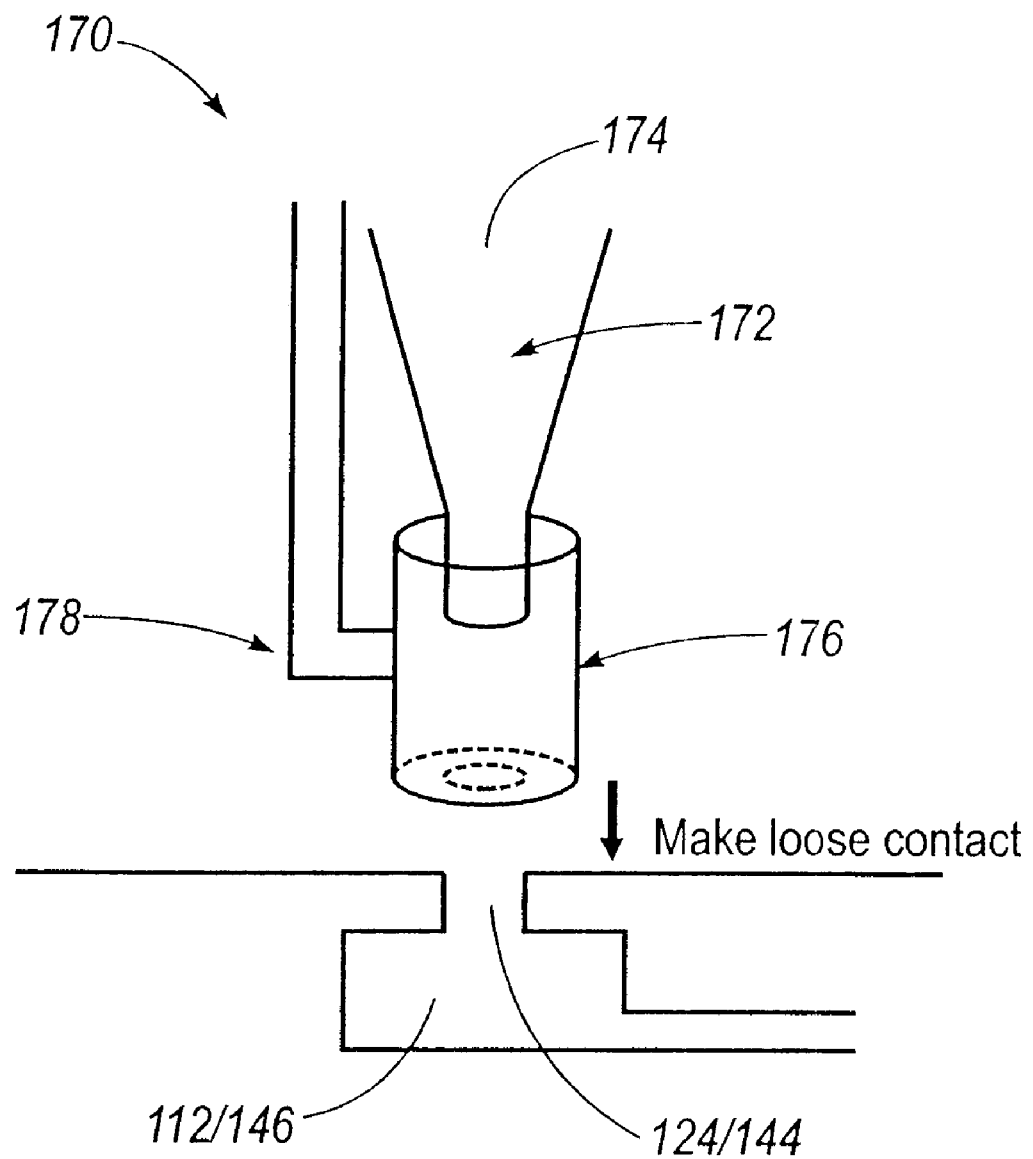
FIG. 16 sets forth a disposable primer connection used in connection with the single and two piece piezoelectric drop ejection mechanisms.

FIG. 16 illustrates a primer connection 170 which may be used in accordance with the present invention. As shown in FIG. 16, the primer connection 170 is located over a nozzle (124, 144) which is configured to emit biofluid from an ejection reservoir (112, 146). In operation, primer connection 170 may be a robodticly actuated device which moves over an ejection nozzle (124/144). The primer connection 170 includes a permanent nozzle 172 connected to a vacuum unit 174. Placed around permanent nozzle 172 is a disposable tubing 176 made of an elastomaric or other suitable connection material. Once located over ejection nozzle (124, 144), the vacuum nozzle 172 is moved downward, placing the disposable tubing 176 into a loose contact with nozzle (124, 144) vacuuming action vacuums air out of the ejection reservoir (112, 146). A liquid height detection sensor 178 determines when the biofluid has reached a level within the disposable tubing (124, 144), such that it is ensured air within the ejection reservoir has been removed. This priming operation permits proper initial drop ejection operation.

While in the foregoing discussion an aperture plate or lid 44 is shown as being used in connection with the acoustic drop ejection mechanisms, the invention may also be employed where the aperture plate of lid 44 is not used. These embodiments may clearly be understood by removal of the aperture plate or lid 44 shown in the foregoing figures. It is intended that the present application covers such embodiments.

It is to be appreciated that while the forgoing description sets forth embodiments for acoustic drop ejection units and piezoelectric drop ejection units, the concepts of the present invention may be equally extended to other drop ejection mechanisms and for fluid other than biofluids for which avoidance of contamination is beneficial, such as printing of inks where isolation from other inks is desirable. Also, the individual ejectors are of a small enough size to make practical the intended use in multi-ejector systems. Such systems would include a drop ejector head having from a hundred to a thousand or more individual drop ejectors.

It is to be further understood that while the figures in the above description illustrate the present invention, they are exemplary only. Others will recognize numerous modifications and adaptations of the illustrated embodiments which are in accord with the principles of the present invention. Therefore, the scope of the present invention is to be defined by the appended claims.

Having thus described the preferred embodiments, what is claimed is:

1. A biofluid drop ejection unit for ejecting biofluid drops, the unit comprising:
   a biofluid drop ejection mechanism having a transducer which generates energy used to emit biofluid drops; and
   a reagent cartridge composed of a biochemically inert material for holding a biofluid, isolated from the drop ejection mechanism to avoid contamination between the biofluid drop ejection mechanism and the biofluid of the reagent cartridge, the reagent cartridge designed to be held in a detachable operative connection with the drop ejection mechanism such that upon operation of the drop ejection mechanism, the biofluid is emitted as the biofluid drops, wherein the reagent cartridge is configured to be disposable and the biofluid ejection mechanism is configured to be reusable; and
   an interior chamber configured to receive the reagent cartridge.

2. The invention according to claim 1 wherein the biofluid drop ejection mechanism is an acoustic drop ejection mechanism.

3. The invention according to claim 1 wherein the biofluid drop ejection mechanism is a piezoelectric drop ejection mechanism.

4. The invention according to claim 1, wherein the interior chamber includes sidewalls and further including:
   a fluid coupling layer located within the chamber to enable energy transmission from the biofluid ejection mechanism to the biofluid in the reagent cartridge; and
   a sealing element on a sidewall of the reagent cartridge, the sealing element configured to engage the sidewalls of the interior chamber to form a seal between the sidewalls of the interior chamber and the sealing element, wherein the sealing element maintains the coupling layer within the interior chamber upon insertion of the reagent cartridge.

5. The invention according to claim 4 further including a controllable power source connected to the transducer, wherein changes to the controllable power source changes the energy generated by the transducer.

6. The invention according to claim 4, wherein the fluid coupling layer is at least one of water and grease.

7. The invention according to claim 1 wherein the biofluid drop ejection mechanism includes:
   a substrate attached to the transducer, wherein the energy generated by the transducer is acoustic energy transmitted through the substrate; and
   a lens mechanism positioned in relationship to the transducer, to receive and focus the acoustic energy at a focal point at a surface of the biofluid held within the reagent cartridge, wherein the focused acoustic energy causes the drops of biofluid to be emitted.

8. The invention according to claim 7 wherein the lens mechanism is carried on a surface of the substrate opposite that of the surface attached to the transducer.

9. The invention according to claim 7 wherein the lens mechanism is carried on the reagent cartridge.

10. The invention according to claim 7 wherein the lens mechanism is at least one of a fresnel lens mechanism and a curved lens mechanism.

11. The invention according to claim 1 wherein the drop ejection mechanism is a piezoelectric drop ejector including,
    the transducer being a piezoelectric actuator;
    the reagent cartridge having at least one surface with a first flexible membrane, which is in operative connection with the piezoelectric transducer; and
    a nozzle in operative connection with the reagent cartridge and positioned in relationship to the piezoelectric transducer such that action of the piezoelectric transducer causes the biofluid to be emitted through the nozzle as the biofluid drops.

12. The invention according to claim 11 wherein the piezoelectric drop ejection mechanism further includes a second flexible membrane in operative connection to a surface of the piezoelectric transducer.

13. The invention according to claim 1 wherein the emitted biofluid drops are part of a biological assay.

14. The invention according to claim 1 wherein reagent cartridge has a top-sealed surface, wherein the sealed surface is opened prior to operation of the biofluid drop ejection mechanism.

15. The invention according to claim 1 wherein a surface of the reagent cartridge from which the biofluid drops are emitted can be either completely open or contained by a lid with an appropriately sized orifice, the orifice being larger than the ejected drop size, and small enough to where a surface tension of the biofluid across the orifice sufficiently exceeds the gravitational force to prevent the biofluid from falling from the reagent cartridge when the reagent cartridge is placed with the orifice facing down.

16. The invention according to claim 1, further including,
    a precision depth stop within the interior chamber designed to position the reagent cartridge at a predetermined insertion location in relationship to the biofluid ejection mechanisms for drop ejection operations.

17. The invention according to claim 1, wherein the interior chamber includes a plurality of sidewalls.

18. The invention according to claim 1, wherein the drop ejection mechanism further includes a lens mechanism, wherein the transducer is formed directly on the lens mechanism.

19. A biofluid drop ejection unit for ejecting biofluid drops, the unit comprising:
    a biofluid drop ejection mechanism having a transducer which generates energy used to emit biofluid drops;
    a detachable reagent cartridge, holding the biofluid in a contamination-free state, the reagent cartridge designed for detachable operative connection with the drop ejection mechanism, wherein upon operation of the drop ejection mechanism the biofluid is emitted as the biofluid drops; and an interior chamber sized to receive the reagent cartridge, the interior chamber including a precision depth stop to position the reagent cartridge at a predetermined location in relationship to the biofluid drop ejection mechanism for drop ejection operation.

20. The invention according to claim 19 wherein the biofluid drop ejection mechanism is at least one of an acoustic drop ejection mechanism having an focused output and a piezoelectric drop ejection mechanism having a nozzle output.

* * * * *